(12) United States Patent
Tanigami (10) Patent No.: US 10,226,272 B2
(45) Date of Patent: Mar. 12, 2019

(54) ARTHROSCOPIC SURGERY METHOD FOR OSTEOCHONDRITIS DISSECANS OF TALUS

(71) Applicant: OLYMPUS CORPORATION, Tokyo (JP)

(72) Inventor: Yasuo Tanigami, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 358 days.

(21) Appl. No.: 15/085,755

(22) Filed: Mar. 30, 2016

(65) Prior Publication Data
US 2017/0172611 A1    Jun. 22, 2017

Related U.S. Application Data

(60) Provisional application No. 62/269,624, filed on Dec. 18, 2015.

(51) Int. Cl.
| *A61B 17/56* | (2006.01) |
| *A61B 17/32* | (2006.01) |
| *A61B 17/16* | (2006.01) |
| *A61B 17/3205* | (2006.01) |

(52) U.S. Cl.
CPC .. *A61B 17/320068* (2013.01); *A61B 17/1682* (2013.01); *A61B 17/32053* (2013.01); *A61B 2017/320078* (2017.08); *A61B 2017/564* (2013.01)

(58) Field of Classification Search
CPC .............................................. A61B 17/320068
See application file for complete search history.

(56) References Cited

U.S. PATENT DOCUMENTS

| 8,652,148 B2 * | 2/2014 | Zuhars ................ A61F 2/30756 600/426 |
| 9,433,471 B2 * | 9/2016 | Zuhars ................ A61F 2/30756 |
| 2007/0275348 A1 * | 11/2007 | Lemon ..................... A61C 3/03 433/119 |
| 2008/0249632 A1 * | 10/2008 | Stone ........................ A61F 2/28 623/23.5 |
| 2011/0208256 A1 * | 8/2011 | Zuhars ................ A61F 2/30756 606/86 R |
| 2012/0310248 A1 * | 12/2012 | Govaers ............. A61B 17/1717 606/87 |
| 2014/0135857 A1 * | 5/2014 | Zuhars ................ A61F 2/30756 606/86 R |
| 2016/0338778 A1 * | 11/2016 | Zuhars ................ A61F 2/30756 |

* cited by examiner

*Primary Examiner* — Zade Coley
(74) *Attorney, Agent, or Firm* — Oliff PLC (57) ABSTRACT

The therapeutic method of an arthroscopic surgery method for osteochondritis dissecans or osteochondral lesion of a talus of the embodiment carries out the cutting treatment safely, without being able to avoid non-treatment target region, being able to reach a treatment target region and doing damage to any peripheral tissues, when performing a treatment since an ultrasonic treatment device is used.

6 Claims, 7 Drawing Sheets

ARTHROSCOPIC SURGERY METHOD FOR OSTEOCHONDRITIS DISSECANS OF TALUS

CROSS-REFERENCE TO RELATED APPLICATIONS

This application is based upon and claims the benefit of priority from the prior U.S. Provisional Application No. 62/269,624 filed Dec. 18, 2015, the entire contents of which are incorporated herein by reference.

BACKGROUND OF THE INVENTION

1. Field of the Invention

The present invention relates to an arthroscopic surgery method for osteochondritis dissecans and osteochondral lesion of a talus in which an ultrasonic treatment device is used.

2. Description of the Related Art

Generally in an arthroscopic surgery, two or three of portals which are small holes are made around a joint (in a skin surface), and an arthroscope made of a hard mirror, a medical treatment device and the like are inserted through these portals. Then, in a state where the joint is filled with irrigation fluid such as saline, the surgery is carried out while confirming an image reflected in a monitor.

Figure 9:
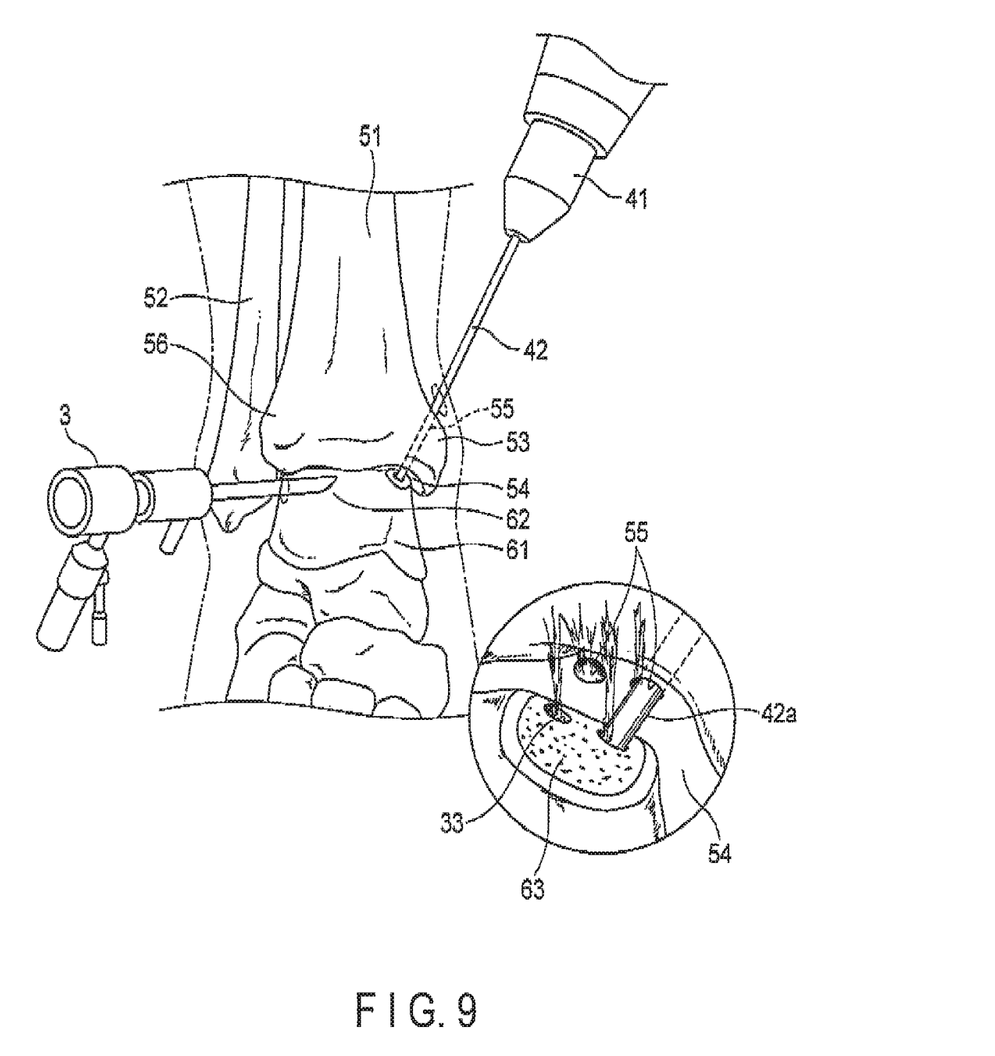
FIG. 9 is a view showing a state where a hole is made in a medial malleolus with a drill blade of a drill to approach a treatment target region of an upper surface of the talus.

In the arthroscopic surgery in which such a conventional medical treatment device is used, anxious problems are present in several treatments. For example, in a case where a drill or the like is used in making a bone hole, the hole is made only in an advancing direction of a drill blade, and hence in a case where the bone hole is made in the joint, an introducing direction is restricted by a position of a treatment target region. That is, in a case where a treatment target is present on the side of a side surface of a talus and the drill blade is approachable to the treatment target from a lateral side, problems do not comparatively occur, but, for example, in a case where a treatment target region 63 is present on the side of an upper surface of a talus 61 as shown in FIG. 9, a portal is prepared above a medial malleolus 53 and a drill blade 42 of a drill 41 is to approach obliquely from above. As a result, a hole 55 is made in the medial malleolus 53 of a tibia 51, and thus there occurs a trouble that causes damages.

Additionally, as treatment tools for use in a conventional arthroscopic surgery or the like, there are a shaver that performs resection and suction of a soft tissue, a burr ablator to shave a bone, and the like. Additionally, there is an ablator in which bleeding of the soft tissue is stopped by using a radiofrequency (RF). In these tools, the bone is shaved while mechanically rotating a grinding region, whereby unevenness remains in a treated surface and it is not easy to smoothen the surface. Additionally, the treatment is carried out by using the radiofrequency, an thus there occurs an anxious trouble that causes thermal damages to a tissue of the treatment target.

BRIEF SUMMARY OF THE INVENTION

According to an embodiment of the present invention, there is provided an arthroscopic surgery method for osteochondritis dissecans or osteochondral lesion of a talus comprising: an ultrasonic probe inserting step of inserting an ultrasonic probe into a treatment target region positioned in a clearance between the talus and a medial malleolus in a direction from tips of toes along the clearance, the ultrasonic probe comprising a long inserting portion and a treating portion disposed on a distal side of the inserting portion and bent in a longitudinal axis direction; a cartilage removing step of removing a cartilage of the talus; a contact step of bringing a distal end of the bent treating portion into contact with a region removed in the cartilage removing step; and a drilling step of forming a bone hole in the removed region by using ultrasonic vibration at the distal end contacted in the contact step Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE PREFERRED EMBODIMENT

Hereinafter, with reference to the drawings, there will be described an arthroscopic surgery method for osteochondritis dissecans or osteochondral lesion of a talus in which an ultrasonic treatment device is used according to an embodiment of the present invention.

According to the present embodiment, there is provided a method of treating the osteochondral lesion or osteochondritis dissecans of the talus by use of the ultrasonic treatment device. Here, the arthroscopic surgery method for the osteochondral lesion of the talus will be described as an example.

In general, the osteochondral lesion of the talus is known as lesion caused by a sprain or the like when an ankle is twisted. Additionally, the osteochondritis dissecans is known as lesion which is easy to be caused to a person who repeatedly performs exercises.

Figure 2:
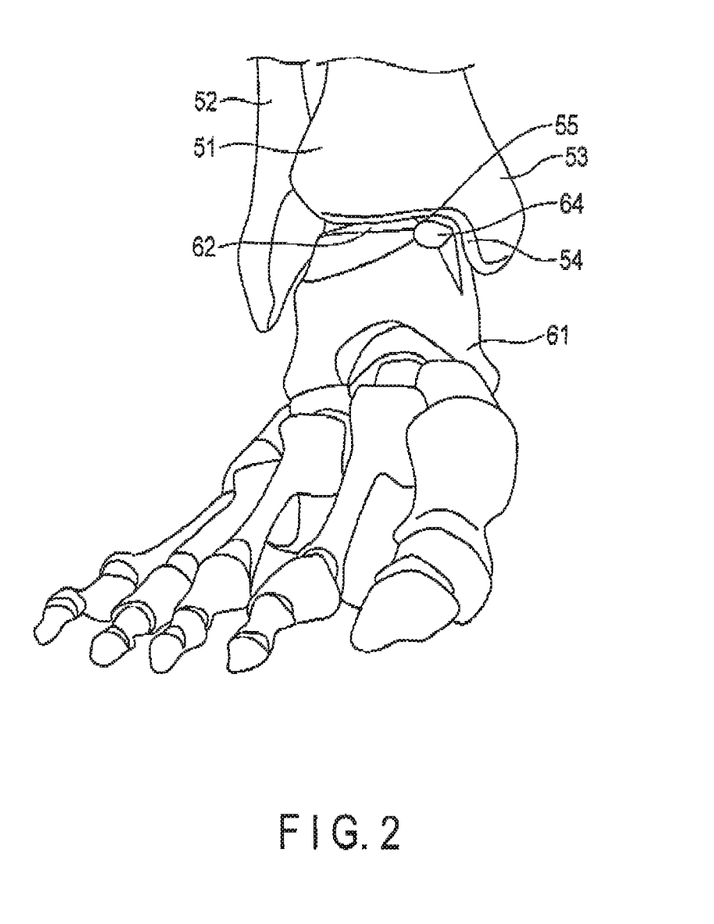
FIG. 2 is a view to explain the osteochondral lesion of the talus.

FIG. 2 is a view to explain the osteochondral lesion of the talus. This osteochondral lesion of the talus is usually the lesion generated in a lesioned region 64 on an inner upper surface of a talus trochlea 62 of a talus 61 that faces a tibia 51, and most of the lesions easily occur due to chronic stress onto an ankle or after the sprain of the ankle (outer ligament lesion), and as a symptom, lack of blood flow or partial peel-off of cartilages including a joint cartilage is caused in a part of the talus 61.

Figure 1:
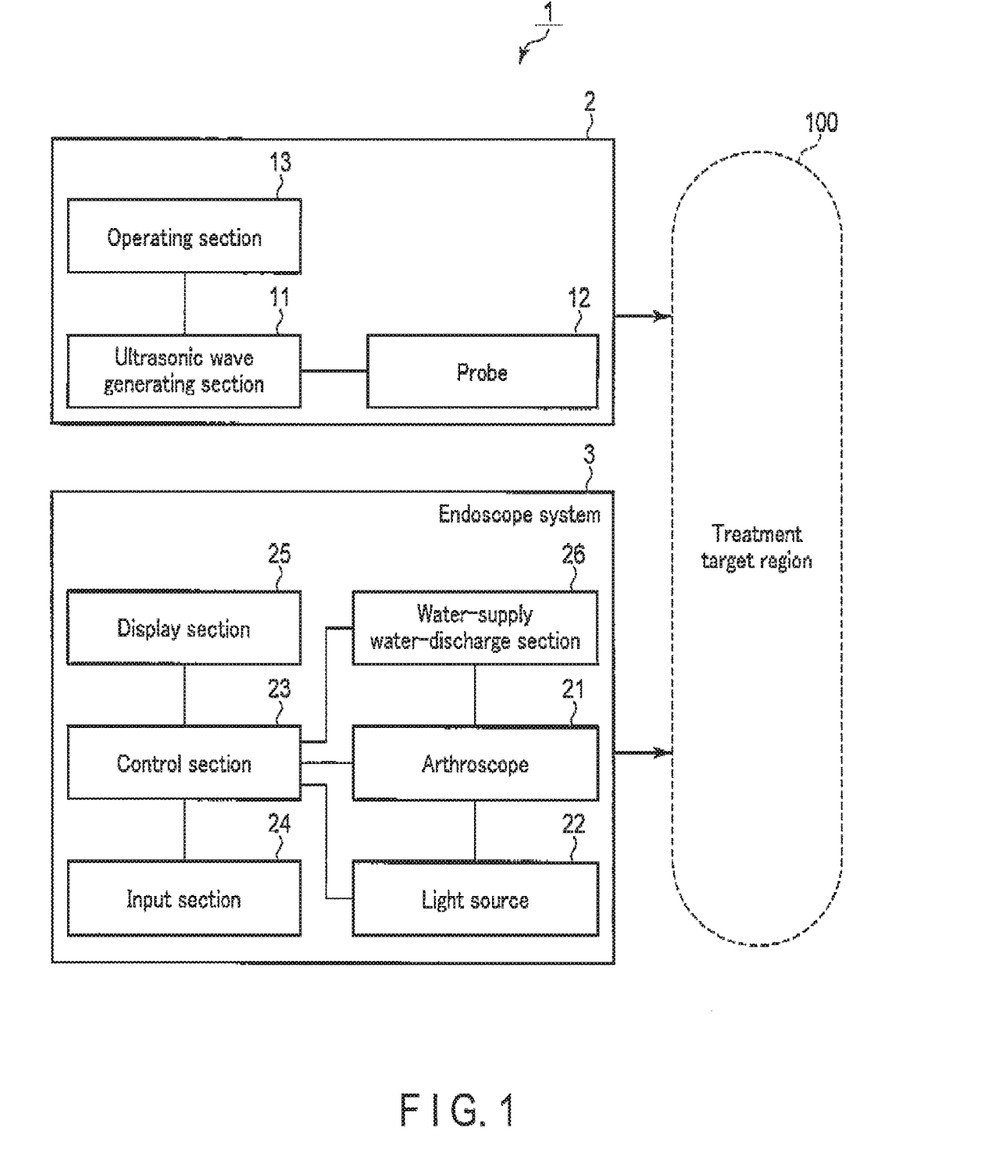
FIG. 1 is a diagram showing a constitution example of a surgical system comprising an ultrasonic treatment device to carry out an arthroscopic surgery method for osteochondral lesion of a talus according to the present embodiment.
Figure 3:
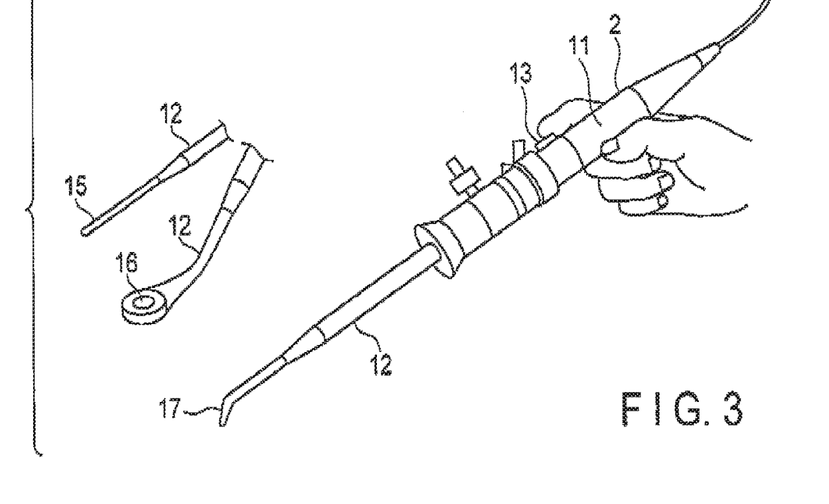
FIG. 3 is a view showing an appearance constitution of the ultrasonic treatment device.

FIG. 1 shows a constitution example of a surgical system comprising the ultrasonic treatment device to carry out the arthroscopic surgery method for the osteochondral lesion of the talus (or the osteochondritis dissecans) according to the present embodiment FIG. 3 is a view showing an appearance constitution of the ultrasonic treatment device. Hereinafter, in the present embodiment, the talus will be described as one example of a treatment target region 100, but the region is not limited to the talus, and it is possible to easily carry out a surgery of similar lesion of another region by use of the ultrasonic treatment device.

A surgical system 1 of the present embodiment is constituted of an ultrasonic treatment device 2 and an endoscope system 3 including an arthroscope 21.

The ultrasonic treatment device 2 comprises an ultrasonic wave generating section 11 that generates ultrasonic vibration by an ultrasonic vibration element (e.g., a piezoelectric element) disposed inside, an ultrasonic probe 12 that transmits the ultrasonic vibration to perform a cutting treatment of the treatment target region 100, and an operating section 13 that drives and controls the ultrasonic wave generating section 11 to perform an on/off operation of the generation of the ultrasonic vibration.

In the ultrasonic treatment device 2 of the present embodiment, treating portions having different functions are disposed on a distal side of the ultrasonic probe 12, whereby portal preparation, cutting of the cartilage and the bone or drilling into the bone can be performed. In the present embodiment, for example, as shown in FIG. 3, an ultrasonic trocar 15, an ultrasonic curette 16 and an ultrasonic drilling portion 17 are used. A distal side of each of the ultrasonic curette 16 and the ultrasonic drilling portion 17 is formed into a bent shape so that a treatment can be carried out in a narrow space.

Figure 4A:
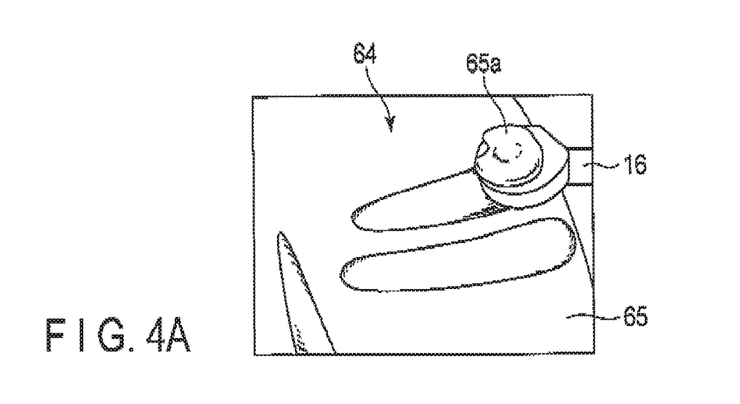
FIG. 4A is a view showing a behavior of cutting a cartilage with an ultrasonic curette.
Figure 4B:
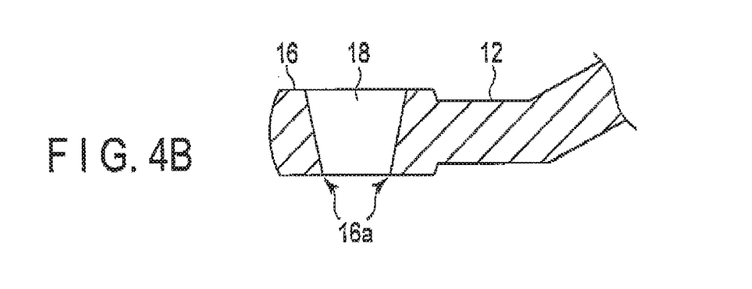
FIG. 4B is a view showing a constitution of a cutting portion of the ultrasonic curette.

As shown in FIG. 4B, the ultrasonic curette 16 includes a cutting portion 18 comprising a frustoconical hole inverted on the distal side. At an edge of an upper bottom (a portion that comes in contact with the cartilage) of a bore of the cutting portion 18, a cutting edge (a cutting blade) 17a is disposed. As shown in FIG. 4A, when the ultrasonically vibrated ultrasonic curette 16 is only lightly pressed against a cartilage 65 of the lesioned region 64, the edge 17a bites into the cartilage 65, so that the cartilage can smoothly be cut. A cut cartilage piece 65a is discharged from an upper opening of the cutting portion 18 to the outside together with circulating irrigation fluid. In particular, the ultrasonic vibration is utilized, and hence, as compared with a conventional treatment tool utilizing a radiofrequency, decrease of heat invasions is achieved.

As the treating portion for use in drilling, there is a treating portion comprising the drilling portion 17 that bends in its middle and has a pointed tip. By ultrasonically vibrating the ultrasonic probe 12 comprising the drilling portion 17, bone holes 33 are made to reach a subchondral bone plate or a cancellous bone, which slightly causes bleeding from the inside onto a bone surface.

Figure 6:
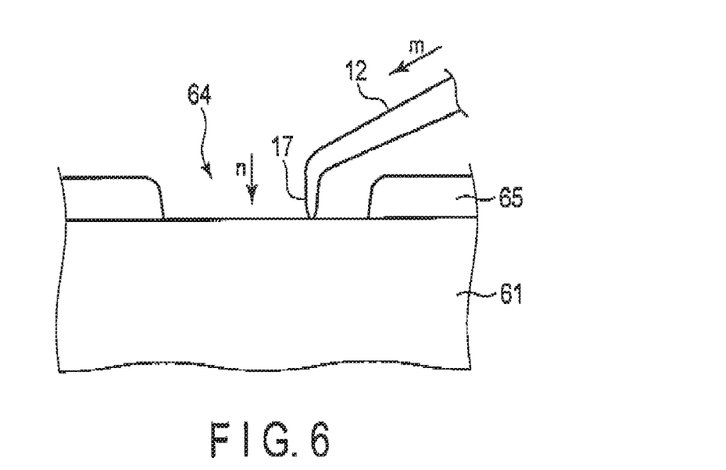
FIG. 6 is a view showing a state where a bone hole is made in a lower bone plate of the talus from which the cartilage is peeled, with a treating portion of an ultrasonically vibrating ultrasonic probe.

As shown in FIG. 6, a distal end of the ultrasonic drilling portion 17 is bent, and hence unlike a drill, the drilling portion is not moved by giving force to a main body of the ultrasonic treatment device 2 in its longitudinal axis direction m, but the drilling portion is moved in a direction n intersecting the longitudinal axis direction. Therefore, even in the case where a joint fissure gap between the talus 6 and the tibia 51 is narrow, hole making can easily be performed when the distal end of the drilling portion 17 is only placed in the joint fissure gap.

The endoscope system 3 is constituted of the arthroscope 21 made of a hard mirror that is one type of endoscope, a light source 22 that is a light source of illumination light for irradiation with the illumination light of visible light, a control section 23 that controls the whole endoscope system 3, an input section 24 such as a keyboard or a touch panel, a display section 25 that displays surgical information including a photographed surgical situation, and a water-supply water-discharge section 26 that supplies, discharges or circulates the irrigation fluid including saline in a periphery of the talus 61 of the treatment object region 100.

In the present embodiment, the water-supply water-discharge section 26 supplies the irrigation fluid to a treatment region through the arthroscope 21 and discharges the irrigation fluid from the region through the arthroscope, but the irrigation fluid may be supplied and discharged by the ultrasonic treatment device 2.

Next, the arthroscopic surgery method for the osteochondral lesion of the talus will be described with reference to FIG. 5 to FIG. 10.

Figure 5:
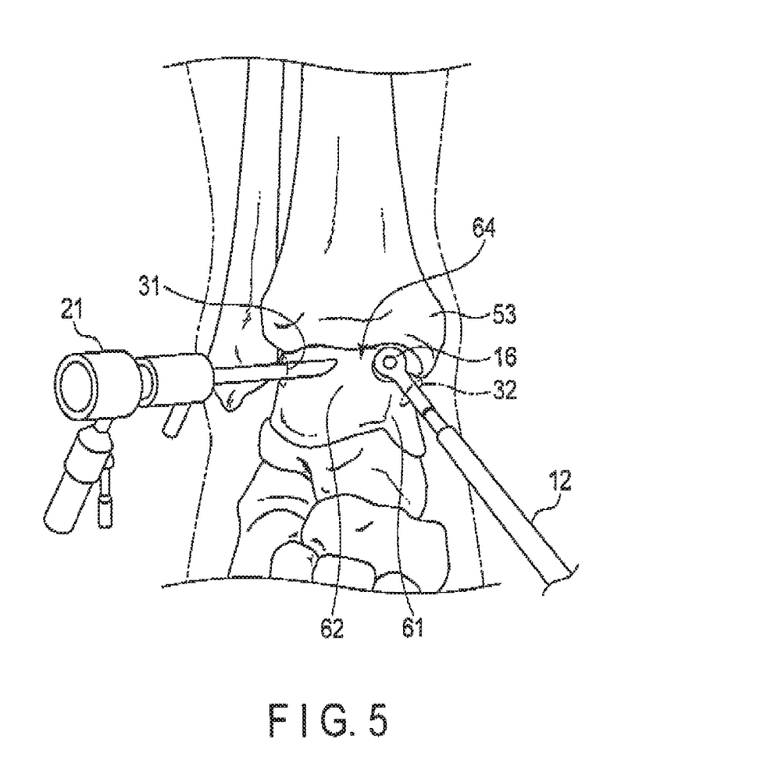
FIG. 5 is a view showing a state to remove a bone soft tissue or the like by an arthroscope and the ultrasonic treatment device which are inserted in a joint.
Figure 7:
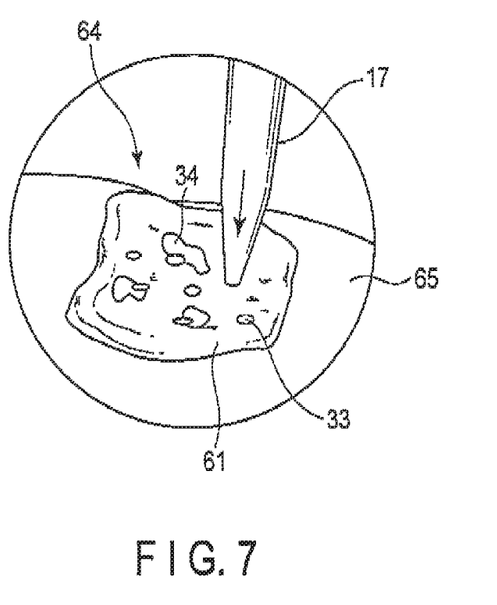
FIG. 7 is a view showing a state where bone holes are made to cause bleeding.
Figure 8:
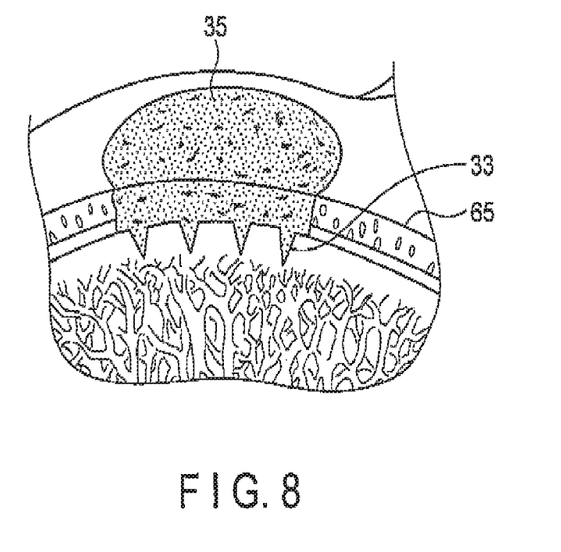
FIG. 8 is a view conceptually showing a state where a cartilage region is reconstructed.
Figure 10:
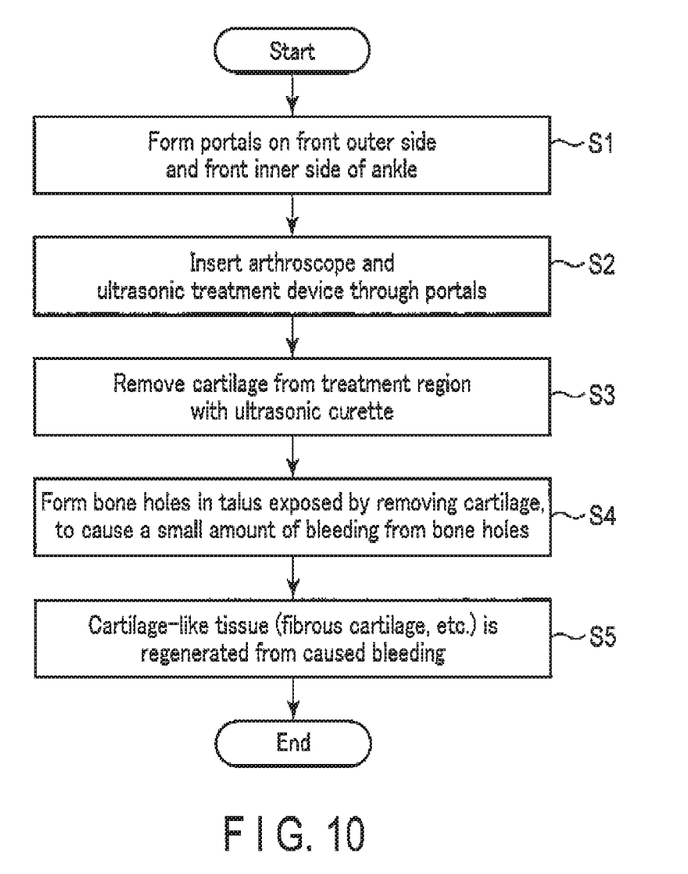
FIG. 10 is a flowchart to explain a procedure of the arthroscopic surgery method for the osteochondral lesion of the talus in which the ultrasonic treatment device is used.

FIG. 5 is a view showing a state to remove a bone soft tissue or the like by the arthroscope and the ultrasonic treatment device which are inserted in a joint. FIG. 6 is a view showing a state where a bone hole is made in a lower bone plate of the talus from which the cartilage is peeled, with the treating portion of the ultrasonically vibrating ultrasonic probe. FIG. 7 is a view showing a state where the bone holes are made to cause the bleeding. FIG. 8 is a view conceptually showing a state where a cartilage region is reconstructed. FIG. 10 is a flowchart to explain a procedure of the arthroscopic surgery method for the osteochondral lesion of the talus in which the ultrasonic treatment device is used.

The ultrasonic trocar 15 shown in FIG. 3 is used, and the ultrasonic vibration is transmitted to a distal portion of the ultrasonic probe 12, so that a biological tissue is coagulated and incised to form portals 31 and 32 on a front outer side and a front inner side between the talus 61 and the tibia 51 (step S1).

The ultrasonic trocar 15 is used for the formation of the portals 31 and 32, so that the bleeding that is easy to occur during the formation of the portals can be inhibited, tenting can be prevented and nerves can be prevented from being damaged. It is to be noted that loads on the ultrasonic trocar 15 due to contact with the biological tissue of a treatment target by the ultrasonic vibration are noticeably decreased, which enables piercing with a small amount of the force. Additionally, the bleeding from the treatment region can be alleviated by a coagulating operation.

Next, the arthroscope 21 is inserted through the portal 31 and the ultrasonic probe 12 of the ultrasonic treatment device 2 is inserted through the portal 32 (step S2).

Next, as shown in FIG. 5, by using the ultrasonic curette 16 of the treating portion for the lesioned region 64, the cartilage 65 is removed (step S3). When the ultrasonic curette 16 is used, the cutting is enabled with high accuracy, and the cartilage can smoothly be cut. In particular, the ultrasonic vibration is utilized, and hence, as compared with the conventional treatment tool utilizing the radiofrequency, the decrease of the heat invasions is achieved. Additionally, not only the cartilage 65 but also the subchondral bone plate can be cut with the ultrasonic curette 16.

Afterward, as shown in FIG. 6, by using the ultrasonic probe 12 comprising the ultrasonic drilling portion 17 as the treating portion, as shown in FIG. 7, the bone holes 33 are formed to reach the subchondral bone plate or the cancellous bone, in the talus 61 exposed in the lesioned region 64 of the treatment region, and marrow under a cartilage tissue is stimulated, thereby causing a small amount of bleeding 34 from the bone holes 33 (step S4).

As shown in FIG. 8, by stimulating marrow under the cartilage tissue (microfracture or drilling), a cartilage-like tissue (a fibrous cartilage, etc.) 35 is regenerated from the caused bleeding (step S5).

As described above, in the present embodiment, when the ultrasonic treatment device is used, the cartilage tissue is removed by using the ultrasonic curette 16, and the small-diameter hole is directly formed in the subchondral bone plate via no medial malleolus of the tibia by using the drilling portion that is bent on its distal side, has the pointed tip and ultrasonically vibrates. Heretofore, during the drilling in the subchondral bone plate, the drill has been used as the treatment tool, and in this case, the medial malleolus of the tibia has to be pierced and the subchondral bone plate has to be reached. On the other hand, in the present embodiment, the medial malleolus of the tibia is not pierced, and hence the medial malleolus can be prevented from being wastefully damaged.

Additionally, unlike the conventional treatment tool in which a rotating drill blade is used, the treating portion of the ultrasonic treatment device is only fixed and ultrasonically vibrated, so that the cutting treatment can more safely be carried out without involving any peripheral tissues of the treatment target by the rotation.

The ultrasonic treatment device of the present embodiment mentioned above has the following operations and effects.

Firstly, the ultrasonic treatment device is not limited to a straight probe structure unlike the drill, the ultrasonic treatment device can optionally be prepared into a bent shape and prepared in accordance with a condition of the treatment target region, the device is therefore capable of easily carrying out the treatment of a region that has not been directly accessible by the conventional treatment tool, and the device is excellent in accessibility.

Secondly, a shape of the treating portion of the ultrasonic probe can be thin, its thickness can be decreased, and its cross section is not limited to a round shape, unlike the drill. The shape of the treating portion of the ultrasonic probe can be selected, whereby the ultrasonic probe has various functions of the ultrasonic trocar, the ultrasonic curette, the ultrasonic drilling portion and the like. Additionally, when a shape of the ultrasonic curette is contrived to have, for example, a bore including a cutting edge or a groove, it is possible to perform not only cutting and peeling of the cartilage tissue but also cutting of the subchondral bone plate, and thus the ultrasonic probe can easily be provided with versatility.

Thirdly, in the ultrasonically vibrating treatment device, an amount of the region to be cut can easily be adjusted by adjusting a degree of pressing by an operator, the cut surface can be smoothened, and a postoperative progress can suitably be obtained. Furthermore, the surface is thus cut by the ultrasonic vibration, so that thermal damages to a treated region can be decreased, the postoperative progress can suitably be obtained, and the device is excellent in less invasive properties.

Fourthly, according to the ultrasonic treatment device, both the soft tissue and a hard tissue can be treated, so that replacing operations of the treating portions can be decreased, and burdens on the operator can be decreased.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An arthroscopic surgery method for osteochondritis dissecans or osteochondral lesion of a talus comprising:
    an ultrasonic probe inserting step of inserting an ultrasonic probe, which has (1) an elongated shaft with a longitudinal axis and (2) a bent treating portion at a distal end of the elongated shaft at an angle with the longitudinal axis, into a treatment target region positioned in a clearance between the talus and a medial malleolus in a first direction from tips of toes towards the talus;
    a cartilage removing step of cutting and removing cartilage of the talus located in a position contacted by the bent treating portion;
    a drilling step of forming a bone hole in a portion of the talus from which the cartilage is removed by using ultrasonic vibration at the bent treating portion, the bone hole extending to a subchondral bone plate or a cancellous bone of the talus;
    a step of stimulating marrow under the cartilage and guiding a small amount of blood, through the bone hole, to the portion of the talus from which the cartilage is removed; and
    regenerating cartilage-like tissue from the blood after the removing cartilage step.

2. The arthroscopic surgery method for the osteochondritis dissecans or osteochondral lesion of the talus according to claim 1,
    wherein in the cartilage removing step, the cartilage is cut and removed by an edge of a cutting portion that is disposed on the distal side of an ultrasonic curette and that ultrasonically vibrates.

3. The arthroscopic surgery method for the osteochondritis dissecans or osteochondral lesion of the talus according to claim 1,
    wherein in the drilling step, the treating portion is a drilling portion having a pointed tip, and with the aid of the ultrasonic vibration, the drilling portion forms the bone hole which reaches the subchondral bone plate or the cancellous bone, to cause bleeding.

4. An arthroscopic surgery method for osteochondritis dissecans or osteochondral lesion of a talus comprising:
    an ultrasonic probe inserting step of inserting an ultrasonic probe into a treatment target region positioned in a clearance between the talus and a medial malleolus in a first direction from tips of toes towards the talus along the clearance, the ultrasonic probe comprising an elongated shaft having a longitudinal axis and a treating portion disposed on a distal end of the elongated shaft at an angle with the longitudinal axis;

a contact step of bringing a distal end of the treating portion into contact with the treatment target region;

a drilling step of forming a bone hole in the treatment target region by using ultrasonic vibration at the distal end; and regenerating cartilage-like tissue from the blood after the drilling step of forming a bone hole.

5. The arthroscopic surgery method for the osteochondritis dissecans or osteochondral lesion of the talus according to claim 4, wherein in the drilling step, the treating portion is a drilling portion having a pointed tip, and with the aid of the ultrasonic vibration, the drilling portion forms the bone hole which reaches a subchondral bone plate or a cancellous bone of the talus, to cause bleeding.

6. An arthroscopic surgery method for osteochondritis dissecans or osteochondral lesion of a talus of a leg of a patient comprising:

providing an arthroscope and an ultrasonic probe with (1) an elongated shaft and (2) a bent treatment tip at a distal end of the elongated shaft, the bent treatment tip having a distal tissue contact end;

forming first and second portals in the leg of the patient for insertion of the arthroscope and the ultrasonic probe, the portals ending near a treatment target region, the first portal being formed in a first direction from toes of the foot of the leg of the patient towards the talus;

inserting the arthroscope into the second portal and the ultrasonic probe into the first portal until the distal tissue contact end contacts the treatment target region;

removing cartilage at the treatment target region by the ultrasonic probe and forming bone holes in the subchondral bone or the cancellous bone of the talus; and regenerating cartilage-like tissue from the blood after the removing cartilage step.

* * * * *